United States Patent
Hayashi

(10) Patent No.: US 7,273,602 B2
(45) Date of Patent: Sep. 25, 2007

(54) IMMUNOTHERAPY FOR HUMANS

(75) Inventor: Akira Hayashi, 9-5, Tsukumodai 3-chome, Suita-shi, Osaka-fu (JP)

(73) Assignees: Akira Hayashi, Suita (JP); Ichiro Azuma, Sapporo (JP); Kumao Toyoshima, Osaka (JP)

( * ) Notice: Subject to any disclaimer, the term of this patent is extended or adjusted under 35 U.S.C. 154(b) by 21 days.

(21) Appl. No.: 10/484,079

(22) PCT Filed: Jul. 19, 2002

(86) PCT No.: PCT/JP02/07337

§ 371 (c)(1),
(2), (4) Date: Jan. 16, 2004

(87) PCT Pub. No.: WO03/009859

PCT Pub. Date: Feb. 6, 2003

(65) Prior Publication Data

US 2004/0208896 A1 Oct. 21, 2004

(30) Foreign Application Priority Data

Jul. 19, 2001 (JP) ............................. 2001-219852

(51) Int. Cl.
A61K 49/00 (2006.01)
A61K 39/395 (2006.01)
A61K 39/38 (2006.01)
A61K 39/04 (2006.01)

(52) U.S. Cl. ..................... 424/9.2; 424/9.1; 424/130.1; 424/184.1; 424/234.1; 424/248.1; 424/278.1; 435/253.1

(58) Field of Classification Search ................. 424/9.1, 424/9.2, 130.1, 184.1, 234.1, 248.1, 278.1; 435/253.1
See application file for complete search history.

(56) References Cited

U.S. PATENT DOCUMENTS

| 4,503,048 | A | 3/1985 | Cantrell |
| 4,726,947 | A | 2/1988 | Shimada et al. |
| 4,744,984 | A | 5/1988 | Ragland |
| 4,746,511 | A | 5/1988 | Kobatake et al. |
| 6,001,361 | A | 12/1999 | Tan et al. |
| 6,593,096 | B1 | 7/2003 | Hayashi et al. |
| 2003/0108527 | A1 | 6/2003 | Seya et al. |

FOREIGN PATENT DOCUMENTS

| EP | 958826 A1 | 11/1999 |
| EP | 1 097 715 A1 | 5/2001 |
| WO | WO-98/43655 A1 | 10/1998 |
| WO | WO-99/55347 A2 | 11/1999 |
| WO | WO 00/03724 A1 | 1/2000 |

OTHER PUBLICATIONS

C.A. Janeway, Jr., Cold Spring Harbor Symp. Quant. Biol., 54, 1-13 (1989).
R. Medzhitov et al., Cell, 91, 295-298 (Oct. 31, 1997).
Proceedings Amer. Assoc. Cancer Res., 89th Annual Meeting, vol. 39, p. 529, Abstract #3598, A. Hayashi, et al., Independent Use of BCG-CWS Effectively Attacks Lymphnode Metastasis of Cancer (Mar. 28-Apr. 1, 1998).
Proceedings Amer. Assoc. Cancer Res., 90th Annual Meeting, vol. 40, p. 657, Abstract #4333, A. Hayashi, Requirement for costimulatory molecules in effective cancer immunotherapy with BCG-Cell wall skeleton (Apr. 10-14, 1999).
Hayashi et al, Proceedings of the Japan Academy, Series B: Physical and Biological Sciences, 1998, vol. 74, No. 3, pp. 50-55.
Hayashi et al. Proceedings of the Japan Academy, Series B: Physical and Biological Sciences, 1994, vol. 70, No. 10, pp. 205-209.
Hayashi et al, "Complete cure of acute myelocyte leukemia with BCG-cell wall skeleton alone", Journal of Haematology, vol. 102, p. 85.
Database WPI Section Ch, Week 198428 Derment Publications Ltd., London, GB; AN 1984-173727 XP002350966 & JP 59 095220 A (Ajinomoto KK) Jun. 1, 1984.
Seya et al: "Innate immune therapy for cancer. Screen for molecules capable of activating the innate immune system." Advances in Experimental Medicine and Biology, 465 p. 229-237. Ref: 30 Journal Code: 0121103. ISSN: 0065-2598. 2000, XP008054070.
Toyoshima, "Reevaluation of Immunopotentiation Therapy for Canser", Japanese Journal of Cancer and Chemotherapy, 2000, vol. 27, No. 6, pp. 817-823.
H. Akira, "A New Trend of Cancer Immunotherapy: BCG-CWS as a Bridge Between the Innate Immunity and the Acquired", Mol Med, 36, 220-229 (1999) (English Abstract).
Akira Hayashi, "Kenko Shihyo Project Series 40 Gan Vaccine No Sayo Kisaku To Men'eki Ryoho 2 BCG-CWS O Mochiiru Gan Tandoku Men'eke Ryoho 30 Nen No Kiroku", Environment and Health, Oct. 2001, vol. 14, No. 5, pp. 259-270.

Primary Examiner—Rodney P. Swartz
(74) Attorney, Agent, or Firm—Birch, Stewart, Kolasch & Birch, LLP

(57) ABSTRACT

An immunotherapy useful for treating a cancer and/or treating and preventing a microbial infection is provided.

A pharmaceutical composition which comprises a bacterial component as an effective ingredient is disclosed, which is used for immunotherapy in a patient suffering from a cancer or microbial infection, wherein the immunotherapy comprises eradicating the cancer cells or the microorganisms from the lymph nodes of the patient.

4 Claims, No Drawings

IMMUNOTHERAPY FOR HUMANS

CROSS-REFERENCE TO RELATED APPLICATIONS

The present application is the National Phase entry under 35 U.S.C. § 371 of International Application PCT/JP02/07337 filed on Jul. 19, 2002.

IMMUNOTHERAPY FOR HUMANS

1. Field of the Invention

The invention relates to an immunotherapeutic agent, and specifically to an immunotherapeutic agent for cancers and/or microbial infections which comprises a bacterial component as an effective ingredient, and a new immunotherapy using the same.

2. Background Art

Immunotherapeutic agents are in general pharmaceutical compositions that are based on the immunology to improve immune functions in patients, thereby treating cancers or infections.

Conventional immunology focused on adaptive immunity existing only in vertebrates, whereas modem immunology has drawn attention to innate immunity, which recently has been recognized as a defense mechanism effective in all living bodies on the earth (Cold Spring Harbor Symp. Quant. Biol., 54, 1–13, 1989. Cell, 91, 295–298, 1997). Lymph nodes are peripheral lymph tissues that lie between lymph ducts, and play the immune responsive roles activating lymphocytes to catch and process foreign materials that invade through skins from outside or tumor cells that grow in the body.

However, such immune responses are induced in not only lymph nodes, but also in other tissues, and therefore the lymph nodes have not been believed an essential tissue for living bodies. Thus, in the light of the fact that cancer metastasis to lymph nodes is a risk factor for cancer patients as is well known, and the prognosis of the patient with cancer metastasis to lymph nodes is drastically different from that of those without such metastasis. In this connection, the lymph nodes have been usually removed without hesitation together with removing a cancer-carrying tissue (radical lymphadenectomy) as a general thing in conventional surgical operations of cancers.

In other words, although radical lymphadenectomy has been known to induce aftereffects bothering patients such as edema or dysmobility, which should be harmful to "Quality of life" of patients to no small extent, those aftereffects have been considered inevitable in compensation for the curing of cancers, and therefore radical lymphadenectomy has been generally conducted in surgical operations.

Radical lymphadenectomy conventionally conducted is advantageous in removal of lymph nodes that may be a risk factor, and capability to reliably diagnose for the stage of cancer patients subjected to the operation. On the other hand, radical lymphadenectomy has disadvantages that it often induces complications such as edema as mentioned above, and that it imposes excessive burdens in operation-time and -procedure on physicians who conduct an operation. The inventor of the present application has considered that the most important disadvantage of radical lymphadenectomy should be the severely adverse effect on innate-adaptive immunity effective in the whole body of patients, which is brought about by removal of lymph nodes that is an important tissue as connection of innate-adaptive immunity, and by discontinuance of lymph ducts that interface between lymph nodes. Such clinical significance of lymph nodes has not been yet recognized in the field of immunology. Additionally, it may be determined waste to remove a cancer-carrying tissue by surgical operation, when the swelling of the lymph node is severe. The present invention could provide a more preferred treatment for such a case.

Further, cancer patients are in general lower in resistance to infections or the like than healthy humans, and specifically cancer patients have significantly lowered immunocompetence not only just after the surgical operation, but also when subjected to chemotherapy, radiotherapy and the like. The invention also provides prevention and therapeutic treatment for such infections as an important purpose.

DISCLOSURE OF THE INVENTION

Since 1974, the inventor of the present application has utilized a bacterial component, BCG-CWS (cell wall skeleton integrants of BCG), to conduct independently immunotherapy of cancers without any other chemotherapy on about 1,000 cancer patients mainly after surgical operations, and obtained excellent therapeutic results (Proc. Japan Acad., 70, Ser. B, 205–209 (1994), Proc. Japan Acad., 74, Ser. B, 50–56 (1998), WO98/39017, Proc. Amer. Assoc. Cancer. Res., 39, 529, #3598 (1998), Brit. J. Haematol., 102, 85, P-0334 (1998), and the like).

The inventor found that, when conducted without radical lymphadenectomy, the immunotherapy with the bacterial component improves significantly therapeutic results, and makes prevention and treatment for infections possible, thereby being accomplished the present invention. According to the immunotherapy of the present invention, cancer metastasis to lymph nodes is no longer any risk factor for cancer patients, and, in other words, risk for progression of the diseases is drastically decreased. The invention provides an immunotherapy improving therapeutic effects on cancers and/or infections, which comprises using a pharmaceutical composition comprising a bacterial component.

Thus, the invention of the present application provides:

(1) A pharmaceutical composition for treatment or prevention of a cancer and/or a microbial infection comprising a bacterial component as an effective ingredient, wherein said treatment or prevention is caused by eradicating the cancer cells or the microorganisms from the lymph nodes of a patient suffering from a cancer and/or a microbial infection;

(2) The pharmaceutical composition according to (1), wherein the cancer cells or the microorganisms are eradicated by dendritic cells as activated in cutaneous Langerhans cells from a patient;

(3) The pharmaceutical composition according to (1), wherein the cancer cells or the microorganisms are eradicated by activated T cells specific for the cancer cells or the microorganisms in lymph nodes of a patient;

(4) A pharmaceutical composition for treatment or prevention of a cancer in a patient comprising a bacterial component as an effective ingredient, wherein said pharmaceutical composition is administered to the patient concurrently with a surgical operation for removing a cancer-carrying tissue, which surgical operation comprises a non-radical lymphadenectomy in which lymph nodes are not removed;

(5) The pharmaceutical composition according to (4), wherein the administration of said composition is initiated prior to the surgical operation;

(6) A pharmaceutical composition for treatment or prevention of a microbial infection, which comprises a bacterial component as an effective ingredient;

(7) The pharmaceutical composition according to any one of (1) to (3), and (6), wherein the microbial infection is a bacterial or viral infection;

(8) The pharmaceutical composition according to any one of (1) to (7), wherein the bacterial component is a BCG-CWS;

(9) A method for treating a cancer and/or a microbial infection, which comprises administering a pharmaceutical composition comprising a bacterial component as an effective ingredient to a patient, thereby eradicating the cancer cells or the microorganisms at the lymph nodes of the patient; and

(10) A method for treating a cancer in a patient, which comprises using a pharmaceutical composition comprising a bacterial component as an effective ingredient, wherein the method is conducted concurrently with a surgical operation for removing a cancer-carrying tissue, wherein the surgical operation comprises a non-radical lymphadenectomy in which lymph nodes are not removed.

DETAILED DESCRIPTION OF THE INVENTION

During the course of the immunotherapy as mentioned above, the inventor found that the swelling of lymph nodes as developed in the patients should be classified into the three types:

(1) The first type is the swelling of lymph nodes (axillary lymph nodes located at the inoculated side) accompanied with pain and fever, which appears suddenly after the inoculation with BCG-CWS in patients who have been inoculated with BCG-CWS and continued their progress satisfactorily, which swelling sometimes bursts. Histochemical analysis reveals that the lymph nodes show a picture of typical chronic granulomatous inflammation, and that the infiltrations of Langhans giant cells and epithelioid cells resemble the infiltrations as infected with tubercule bacilli. However, there is neither tubercule bacilli nor cancer cells, and no necrotic lesion is found. There is also neither activated dendritic cells nor T cells among the cell components. In this context, this type of lymph node swelling is observed in patients in conditions of almost curing when they show strong response to the inoculation with BCG-CWS, whose prognosis is always good.

(2) The second type is lymph nodes isolated by radical lymphadenectomy from patients who have been receiving the inoculation with BCG-CWS since the pre-operative period. Histochemical analysis reveals that the lymph nodes show a modification that is observed in the lymph nodes without a metastasis from the cancer patients, and that the small amounts of dendritic cells that are activated are infiltrated into the lymph nodes, thus understanding that the lymph nodes should be about to prepare to attack the cancer cells.

(3) Finally, the third type is the swelling as observed in patients who have been receiving the inoculation with BCG-CWS since the pre-operative period similarly to the second type, which is generally indolent, and appears at axillary, cervical, subclavian or supraclavicular lymph nodes about one week after the inoculation. Histochemical analysis reveals that the lymph nodes show a modification that is most commonly observed in the swelled lymph nodes with cancer metastasis, and that the lymph nodes are occupied entirely by cancer cells. The intercellular space is invaded by many activated dendritic cells, and the cancer cells are surrounded and likely attacked by activated T cells that express a co-stimulatory molecule of CD28 or CD152, or perforin on the cell surface, of which some cancer cells fall into necrosis. The activated T cells are understood to be cytotoxic T lymphocytes (CTLs) specific for the cancer cells existing in the lymph nodes, showing that the T cells effectively eradicate the cancer cells in lymph nodes, which provide a special environment. Since merely small amount of this type of the T cells appears in peripheral bloods, lymph ducts interfacing between lymph nodes play an important role. Patients who respond as shown above after the BCG-CWS inoculation usually show a good prognosis, whereas patients who have a distant metastasis do not always show a good prognosis.

What is important in the responses in lymph nodes as mentioned in above (1) to (3), is the fact that activated T cells appear only when cancer cells exist in lymph nodes. In case of (2), T cells have not been yet activated although a sort of activated dendritic cells which have a leading role in innate-immunity surely appears. Any place or site in a living body carrying a cancer has not been yet known where the phagocytosis, the processing, the antigen-presentation and the killing of cancer cells as an antigen occur. Here, the inventor of the present application demonstrates for the first time that lymph nodes of cancer patients provide "a place" where such events occur. Further, the killer T cells produced can be identified as CTLs specific for cancer cells existing in such lymph nodes.

In view of the findings as mentioned above, the inventor assumes that lymph nodes should be extremely important in immunotherapy because the lymph nodes are a "place" where host defense system of patients effectively attacks the cancer cells although the lymph nodes are also a "place" for cancer metastases. In this context, the mechanism of immunotherapy with BCG-CWS is as follows:

1. Langerhans cells are activated by intracutaneous administration of BCG-CWS to form activated dendritic cells.

2. The activated dendritic cells migrate to lymph nodes proximal to a cancer-carrying tissue through lymph ducts.

3. T cells (CTLs) expressing CD28 or CD152 are activated only in the presence of cancer cells at the lymph nodes proximal to a cancer-carrying tissue.

4. The activated T cells effectively attack and eradicate the cancer cells at the lymph nodes proximal to a cancer-carrying tissue.

5. The activated T cells migrate to cancer-carrying tissues and other lymph nodes through lymph ducts so as to attack and eradicate the cancer cells.

The mechanism as described above is supported by the finding that therapies with BCG-CWS are less effective to treat the cancers located at organs such as brain, bone, and sarcoma where no lymph node exists. When survival rate at 5 years of patients with lung cancer (non-small cell cancer) is compared, therapies with BCG-CWS led to even higher survival rate for stages I, II, and III than cancer therapies as conducted conventionally at other hospitals. Further, 5 year-survival rates of patients at stages I and II who were treated with BCG-CWS were in fact almost the same, and both reached 90% or more, suggesting that the therapy using BCG-CWS alone is effective regardless of whether metastasis to lymph nodes is present (Stage II) or absent (Stage I). On the other hand, immunotherapy using BCG-CWS alone led to the same 5 year-survival rates of patients at stages IV as the conventional cancer therapies, suggesting that immunotherapy using BCG-CWS alone would be less effective for a distant metastasis. Although 5 year-survival rates of patients at stage III who were treated with BCG-CWS (61%) were significantly improved compared to that with conventional cancer therapies (22%), the survival rates were lower than those of patients at stage II, which lower survival rates would also be caused by distant metastasis. Those facts do not negate the mechanism of the immunotherapy with BCG-CWS as described above.

Under the present circumstances, cancer immunotherapies with cancer vaccines, adjuvants and the like have not always provided an ensured efficacy in humans although they have been demonstrated effective in experimental animals such as mice. Contrarily, the inventor of the present application demonstrated the efficacy of immunotherapy with BCG-CWS by collecting clinical data of many human patients for the first time, and elucidated the mechanism of this immunotherapy as shown above.

Thus, the present inventor considers that a BCG-CWS-alone immunotherapy significantly improves therapeutic effects when radical lymphadenectomy is not conducted, even if there would be a risk of cancer metastasis.

Further, cancer patients are in general lower in resistance to infections or the like than healthy humans. During the course of the immunotherapy for cancers with BCG-CWS conducted over a long period of time, the inventor found that the patients subjected to the immunotherapy showed improved resistance to various infections. Specifically, examination for bacterial infections revealed that, among 237 patients who were subjected to the immunotherapy with BCG-CWS and survived for 2 years or more, there was each only one case, which was suffered from bacteria pneumonia, and pulmonary tuberculosis, respectively. For viral infections, we obtained some data showing that patients subjected to the immunotherapy with BCG-CWS caught neither influenza nor common cold, which had stricken the patients before the immunotherapy with BCG-CWS twice or three times every year. To the contrary, hepatitis C virus did not disappear in the patients who had suffered from hepatitis C before the immunotherapy with BCG-CWS. However, any hepatic cancer has not been newly developed, and rather the existing hepatic cancer tended to gradually improve.

Additionally, each one patient with lung cancer and with maxillary cancer who has also suffered from methicillin-resistant *Staphylococcus aureus* (MRSA) had continued inflammation at the operated lesion without eradication of the bacteria regardless of use of various antibiotics. Thereafter, the continued immunotherapy with BCG-CWS resulted in whole eradication of bacteria and a complete cure of the wound at the operated site.

Patients with other diseases, and healthy humans also develop these infections with some incidence generally. However, the patients subjected to the immunotherapy with BCG-CWS showed a significantly lowered incidence.

It has been understood that since the immunotherapy with BCG-CWS efficiently attacks cancer cells that are "foreign materials", the immunotherapy could be expected to provide similar therapeutic and preventive effects on the infections of bacteria or viruses as being replaced with the cancer cells, also taking account of the mechanism as described above. Those findings show that the immunotherapy with BCG-CWS should be also effective for treatment and prevention of infections.

Although there has been concern that the immunotherapy with BCG-CWS may cause autoimmune diseases due to overactive immunostimulation, no case has been observed yet.

BEST MODE FOR CARRYING OUT THE INVENTION

As the first embodiment, the present invention typically provides a pharmaceutical composition for treatment or prevention of a cancer in a patient comprising a bacterial component as an effective ingredient, wherein said pharmaceutical composition is administered to the patient concurrently with a non-radical lymphadenectomy. Bacterial components include a dead bacterium, and a CWS derived from a microorganism and a lipopolysaccharide (LPS). Dead bacteria are exemplified by a dead *Mycobacterium tuberculosis* (same as human *tubercle bacillus*), and the like. Microorganisms from which a CWS is derived are exemplified by *Mycobacteriaceae, Nocardiaceae, Corynebacteriaceae*, and the like. Among them, BCG of *Mycobacterium bovis*, and *Nocardia rubra* are preferred. These CWSs may be obtained in form of an insoluble residue through a purification process which comprises crashing the cells with a physical means, removing nucleic acids and proteins from the cell debris, and then delipidating the resultant material, and specifically may be prepared by the process as described in J. Nat. Cancer Inst., 52, 95–101 (J1974).

Dosage form of the liquids of a bacterial component is not limited to particular form, and the bacterial component is preferably administered as an emulsion formed with an oil, a surfactant, a stabilizer or the like, with preferred concentration of the bacterial component being 0.1 to 10 mg/ml. In the present invention, oils include a mineral oil, or an animal and vegetable oil such as those described in Immunology, 27, 311–329 (1974). Specific examples include a liquid petrolatum, a bayol, Drakeol-6VR, squalane, squalene and the like. Surfactant is not limited to a particular species as long as it can be used in a pharmaceutical formulation. It includes a phospholipid, a nonionic surfactant, and the like. Specific examples include Polysorbate 20, Polysorbate 80 and the like. Stabilizer includes a polysaccharide, a monosaccharide, a sugar alcohol, an amino acid, a polyalcohol, a protein, urea, sodium chloride, and the like. Specific examples include cellulose, starch, dextran, glycine, proline, glucose, mannitol, albumin, and the like.

The pharmaceutical composition of the present invention is effective against almost any cancer. For example, the composition may be used for immunotherapy of cancers such as lung cancer, stomach cancer, colon cancer, renal cancer, breast cancer, maxillary cancer, lingual cancer, pharyngeal cancer, acute myeloid leukemia, pancreatic cancer, ovarian cancer, uterine cancer, and prostate cancer.

Typical administration for the effective ingredient according to the present invention is intracutaneous route, and the pharmaceutical composition of the present invention is injected into a patient.

Dose, inoculation schedule, and inoculation site of the effective ingredient of the present invention are not limited to particular ones, and some examples therefor are provided below.

(1) Sensitization phase: each 200 μg of BCG-CWS is intracutaneously inoculated once a week for a total of four times.

(2) Therapeutic phase: an appropriate amount of BCG-CWS depending on biological responses of a patient, as selected from 2 to 200 μg is intracutaneously inoculated every four weeks. For the timing when the sensitization phase is conducted, the inoculation may be initiated either before or after a surgical operation for removing a cancer-carrying tissue, and preferably is initiated about three weeks to about three months before the surgical operation. For frequency of inoculation and number of doses during the initial phase (sensitization phase), it is preferred that inoculation is conducted once a week or every two weeks, and for a total of two to four times. More preferably, inoculation is conducted once a week, totally four times. During the therapeutic phase, continuous inoculation is conducted at a frequency of once every four weeks, and depending on the condition of patients, the frequency of the inoculation may be lowered to once every two to six months for example. Duration time of therapeutic phase is not limited to particular one, and varies depending on each case such as immunocompetency of patients, effect of immunotherapy, progress degree of cancers, and presence or absence of recurrence and distant metastasis. For example, inoculation during therapeutic phase may be conducted over two to ten years. It is important that frequency and dose of inoculation is designed in view of biological responses of a patient, and is varied individually in a wide range. For inoculation site, intracutaneous inoculation is usually conducted alternately either at right or left lateral brachium, and may be conducted at a site nearer to the cancer lesion.

Biological responses as mentioned above include skin reactions such as flare, induration, and formation of ulcer, as well as increased body temperature, increased level of INF-γ in blood, and blood counts of lymphocytes, granulocytes, or the like, and specific biological responses as an index for determining the amount of inoculation are described in WO98/39017, Proc. Japan Acad., 70, Ser. B, 205–209 (1994), Proc. Japan Acad., 74, Ser. B, 50–56 (1998), Molecular Medicine Extra version Vol. 36, "Immunology 1999–2000", pages220 to 229, and the like.

Non-radical lymphadenectomy means any surgical operation for removing a cancer-carrying tissue to treat cancers, in which lymph nodes are not removed. In this context, it is preferable to leave all of lymph nodes if possible, but some part of lymph nodes as located near the cancer-carrying tissue can be removed for diagnosis or depending on the progress degree of cancers, which cases are also fallen within the meaning of non-radical lymphadenectomy as used herein.

In the present embodiment, the invention also provide an immunotherapy, and a method for treating or preventing a cancer, which comprise administering a therapeutically effective amount of a bacterial component to a patient subjected to non-radical lymphadenectomy.

As the second embodiment, the invention provides a pharmaceutical composition for treatment or prevention of an infection, which comprises a bacterial component as an effective ingredient. Infections include a bacterial or viral infection. Bacterial infections include pneumonia, pulmonary tuberculosis, pulmonary emphysema, and MRSA-infections. Viral infections include common cold, influenza, hepatitis B. Also, the invention may prevent cancer caused by hepatitis C.

Patients to be subjected to the present embodiment are not limited to particular ones, and encompass those who are lowered in resistance to infections, particularly patients who have been just subjected to surgical operations, and cancer patients who are undergoing chemotherapy or radiotherapy.

Dose, number and frequency of inoculation of the pharmaceutical composition are not limited, and for example each 5 to 200 μg of BCG-CWS may be inoculated at frequency of once a week to every four weeks, for a total of four times or more. Dose, number and frequency of the inoculation are preferably varied depending on biological responses of a patient.

In the present embodiment, the invention provides a method for treating or preventing an infection, which comprises administering, preferably intracutaneously, a therapeutically effective amount of a bacterial component to a patient in need.

The following examples are presented for purpose of further illustration of the invention, and such examples are not intended to be limiting the invention in any respect.

EXAMPLE 1

Preparation of BCG-CWS Inoculant

BCG-CWS may be prepared according to the method as described in Azuma et al., J. Natl. Cancer Inst. 52:95–101 (1974).

BCG-CWS inoculant may be prepared according to the method as described in Hayashi, A, Proc. Japan Acad.,70, Ser.B(1994). Particularly, the BCG-CWS powder is placed in a 20 mL grinder tube, and a mineral oil (Drakeol-6VR; Pennsylvania Refining Co., Butler, U.S.A.) is added to the tube at a ratio of one drop per 1 mg of BCG-CWS using a 26 G injection needle, after which the mixture is ground to obtain a smooth paste. To the mixture, 1.1% Tween 80 solution in physiological saline is added, and the mixture is then homogenized. The final concentration of a uniform suspension of small oil droplets containing BCG-CWS is 1 mg/mL. The oil attached BCG-CWS suspension was sterilized by incubating at 60° C. for 30 minutes.

EXAMPLE 2

Inoculation Schedule

In principal, BCG-CWS is always inoculated alone.

Inoculation schedule may be divided into sensitization phase and therapeutic phase. In the sensitization phase, usually 200 μg of BCG-CWS is intracutaneously inoculated once a week, totally four times, at the right and left lateral brachiums alternately. During the subsequent therapeutic phase, alternate inoculation is repeated every four weeks. Amount of BCG-CWS to be inoculated is selected from between 20 and 250 μg, preferably between 25 and 200 μg, depending on biological responses of a patient.

EXAMPLE 3

Observations on Lymph Nodes of Patients

Portions of the lymph nodes of cancer patients that had been taken by surgical operation were observed for various immunological markers. The results were summarized as shown below together with clinical findings.

In the following table, (1) to (3) represent the lymph node types as indicated (1) to (3) above, respectively.

(1) shows a status of typical chronic granulomatous inflammation, and neither contained any cancer cells, nor showed any necrotic lesion. Further, there was also neither activated dendritic cell nor T cell that presents a specific co-stimulatory molecule marker. In this context, this type of lymph node swelling was observed in patients in conditions of almost curing when they show strong response to the inoculation with BCG-CWS, whose prognosis was always good.

(2) shows a status of the lymph nodes isolated by surgical operation from a patient who had been inoculated four times with BCG-CWS before the operation, which operation was conducted one month later, in which the lymph node showed a modification that was observed in the lymph nodes without metastasis from cancer patients. The small amounts of dendritic cells that are activated were infiltrated into the lymph node, thus understanding that the lymph node should be about to prepare to attack the cancer cells. The lymph node also did not contain any cancer cells, and therefore usually the prognosis is good. If, however, the primary cancer remains or distant metastasis occurs, then the prognosis is not always good.

(3) shows a modification that was observed in the swelled lymph nodes with cancer metastasis, and represented a lymph nodes swelling that occurred about a week after BCG-CWS was inoculated before the operation or the recurrence. The lymph nodes are entirely occupied by cancer cells. The intercellular space was invaded by many activated dendritic cells, and the cancer cells were surrounded and likely attacked by activated T cells that presented a co-stimulatory molecule, CD28 or CD152, or perform on the cell surface, of which some cancer cells fell into necrosis. The activated T cells were CTLs specific for the cancer cells existing in the lymph node, and effectively eradicated the cancer cells in lymph nodes that provided a special environment. Patients who responded as shown above after the BCG-CWS inoculation usually showed a good prognosis, whereas patients who had a distant metastasis did not always show a good prognosis.

size. Rapid preparation of the specimen revealed no malignant picture, and therefore the removals of uterine and right ovary were continued. After the operation, the permanent preparation demonstrated to be malignant clear cell carcinoma, and she was diagnosed to require a reoperation to remove the lymph nodes (radical lymphadenectomy). However, she desired an immunotherapy and consulted Osaka medical center for Cancer and Cardiovascular Diseases. Since she was good in general conditions, and tumor marker CA125 was 120 U/ml (normal value: 35 or less) and CA19–9 was 199 U/ml (normal value: 37 or less) immediately before the operation, immunotherapy with independent use of BCG-CWS wherein the tumor markers were used as indicator was initiated on the 21th day after the operation in accordance with the inoculation schedule of Example 2 after reconfirming her intention. Subsequently, she has shown good prognosis, and develops no disease at the present even after 6 years or more have passed with keeping the above tumor markers within the normal values.

(2) Case 2: 48 Years Old, Female

Disease: Breast Cancer (Papillary Adenocarcinoma), Stage II (T2aN1bM0)

In agreement with the patient and her family, the immunotherapy with BCG-CWS was conducted according to the inoculation schedule of Example 2 prior to surgical opera-

TABLE 1

| | | (1) | (2) | (3) |
|---|---|---|---|---|
| Clinical findings | | Swellings accompanied by pains, bullosa, and discomfort | None | Indolent swellings |
| Histochemical analysis of lymph nodes | | tuberculous granulomatous like condition without necrosis | Small inflammations Almost normal | Infiltrations of adepithelial cells and tumor cells |
| Markers for antigen | Tubercle bacillus | – | – | – |
| | Cancer cells | – | – | +++ |
| Markers for Dendritic cells | CD1a | – | + | ++ |
| | CD11c | – | ++ | +++ |
| | CD40 | – | ++ | ++ |
| | CD80 | – | + | ++ |
| | CD86 | – | + | ++ |
| Markers for T cells | CD4 | ++ | +++ | ++ |
| | CD8 | + | ++ | +++ |
| | CD28 | – | – | +++ |
| | CD152 | – | – | +++ |
| Markers for NK cells | CD56 | – | – | – |
| Prognosis | | Good | Usually good, but dependent on progress degree and presence of distant metastasis | Usually good except for the presence of distant metastasis |

EXAMPLE 4

Combinations of Therapy of Non-radical Lymphadenectomy and BCG-CWS Immunotherapy (1) Case 1: 60 Years Old, Female Disease: Ovarian Cancer (Clear Cell Carcinoma), Stage Ia (T1aNxMx)

When the surgical operation was conducted for uterus myoma, the right ovary was found to be enlarged to a fist tions for the first time. Since about one week after the initiation of the therapy, painless enlarged lymph nodes having a pea size suddenly appeared, of which the 3 to 4 appeared at the right axillary cavity where no mass had been felt, the 2 to 3 at the right neck, and the one at the right supraclavicular fossa. One month after the initiation of the immunotherapy, surgical operation for the original cancer with non-radical lymphadenectomy was conducted; the original tumor (diameter about 4.5 cm) was removed with one enlarged lymph node newly appeared at right axillary cavity. The removed lymph node was occupied with the metastatic cancer cells, but the immunostaining revealed that the activated dendritic cells (positive for surface markers such as CD1a, CD11c, CD40, CD80, and CD86) infiltrated into the cancer cells, and simultaneously activated T cells (positive for CD28, CD152 marker) surrounded and attacked the tumor cells. Subsequently, she has shown good prognosis, and develops no disease and is healthy at the present after 4 years and 4 months have passed.

(3) Case 3: 28 Years Old, Female

Disease: Cervical Cancer (Small Cell Carcinoma), Clinical Stage Ib (T1bNxM0)

In agreement with the patient and her family, the immunotherapy with BCG-CWS was conducted according to the inoculation schedule of Example 2 prior to surgical operations. After examination of the positive induction of interferon γ, the whole uterus was removed together with a non-radical lymphadenectomy 38 days after the initiation of the immunotherapy. Subsequently, she has shown good prognosis, and develops no disease at the present after 1 year and 10 months have passed, although she was diagnosed before operation to have a survival time of 6 months or less.

(4) Case 4: 50 Years Old, Female

Disease: Breast Cancer (Infiltrative Mammary Duct Cancer), Clinical Stage IIIa (T3NxM0)

In agreement with the patient and her family, the immunotherapy with BCG-CWS was initiated according to the inoculation schedule of Example 2 prior to surgical operations, and on the 15th day, the whole primary breast cancer was removed together with a non-radical lymphadenectomy. Subsequently, she has shown good prognosis, and developed neither sequelae nor disease after 1 year and 7 months after treatment.

EXAMPLE 3

Frequency of Infections in Patients Subjected to Immunotherapy with BCG-CWS

Immunotherapy with independent use of BCG-CWS that has been conducted for about 30 years has been found to provide significantly decreased incidences of infection irrespective of the fact that cancer patients in general have a lowered immunocompetence, and are more likely to suffer from infections than healthy humans.

Specifically, Table 2 hereinafter shows the clinical cases of infections that are required to be cured by physicians among 237 clinical cases who survive for two years more since cancer developments. For the bacterial infection, there was each only one case, which is suffered from pneumonia by the standard bacteria, and pulmonary tuberculosis, respectively. Further, for viral infections, we obtained the data showing that the patients caught neither influenza nor common cold, which had stricken the patients before the immunotherapy with BCG-CWS twice or three times every year. To the contrary, hepatitis C virus did not disappear in the patients who had suffered from hepatitis C before the immunotherapy. However, any hepatic cancer has not been newly developed, and rather the existing hepatic cancer tended to gradually change for the better.

TABLE 2

| Cancer Type | Number of cases[1] | Bacterial infection | Tuberculosis | Influenza/common cold[2] | Hepatitis C |
|---|---|---|---|---|---|
| Pulmonary cancer | 117 | 1 | 1 | 0 | 2 |
| Large intestine cancer | 26 | 0 | 0 | 0 | 1 |
| Stomach cancer | 19 | 0 | 0 | 0 | 0 |
| Breast cancer | 14 | 0 | 0 | 0 | 0 |
| Oropharyngeal cancer | 10 | 0 | 0 | 0 | 0 |
| Ovarian cancer | 10 | 0 | 0 | 0 | 0 |
| Renal cancer | 8 | 0 | 0 | 0 | 0 |
| Blood cancer | 7 | 0 | 0 | 0 | 0 |
| Others | 26 | 0 | 0 | 0 | 1 |
| TOTAL | 237 | 1 | 1 | 0 | 4 |

[1] Number of cases who survived for 2 years or more after the inoculation with only BCG-CWS
[2] Cases who developed twice to three times a year before the inoculation with only BCG-CWS

EXAMPLE 4

Cases Who Completely Cured MRSA Infections (1) Case 1 (56 Years Old, Female)

Disease: Maxillary Cancer (Squamous Cell Carcinoma), Stage III (T3bN0M0)

After the surgical operation for the disease, the fistulization was observed near the outer corner of left eye, and MRSA was detected in the transudate. Administration with antibiotics of Cravit, Vancomycin, and Habekacin did not close the fistula completely. The immunotherapy with BCG-CWS was conducted according to the inoculation schedule of Example 2, 6 month after the operation, and the fistula was completely closed 2 to 3 months later, after which any recurrence involving the primary cancer has not been observed.

(2) Case 2 (69 Years Old, Male)

Disease: Pulmonary Cancer (Adenocarcinoma), Stage Ib (T2N0M0)

On may in 1995, the surgical operation for the disease was conducted. Then, he was suspected to have the recurrence, and, in response to his intention, the immunotherapy with BCG-CWS was initiated from March in 1999 according to the inoculation schedule of Example 2. Subsequently, he was almost cured of the pulmonary cancer, but he was indicated to have an increased level of PSA and prostate cancer on May in 2000, thus being subjected to a surgical operation. MRSA bacteria was detected in the fistula formed after the operation, and was resistant to antibiotics of Cravit, Vancomycin, and Habekacin. Two months after the resumption of the immunotherapy with BCG-CWS, any bacteria were not detected and the fistula was closed.

Discussions

A series of materials referred to as BRM (biological response modifier) has been acknowledged, which comprises dead bacteria, and bacterial components such as a cell wall skeleton integrant, muramyl dipeptide (MDP), and a lipopolysaccaride (LPS). It has been known that, among them, the cell wall skeleton integrants of bacteria exhibit an anti-tumor activity in experimental tumor systems and immunotherapy for human cancers, for example (Cancer Res., 33, 2187–2195 (1973), J. Nat. Cancer Inst., 48, 831–835 (1972), J. Bacteriol., 94, 1736–1745 (1967), Gann, 69, 619–626 (1978), J. Bacteriol., 92, 869–879 (1966)). Many therapeutic results that have been demonstrated by immunotherapeutic agents for cancer with bacterial components such as viable bacteria, BCG (Bacille Calmette-Guerin), have been already accumulated.

For example, the therapeutic results include those widely reported including the clinical effects of BCG-immunotherapeutic agents on acute lymphocytic leukemia and on melanoma that were demonstrated by Mathe et al. and by Molton et al. respectively in the latter half of 1960's for the first time. However, BCG-immunotherapeutic agents were not sufficiently effective in clinical results, and they were used only as supplements to chemotherapeutic agents, thus eventually not being practically utilized in the clinical field. In addition to BCG, bacteria such as C. parvum, Hemolytic streptococcus, and OK432 have been also utilized. However, in cancer immunotherapy with those bacteria, some were effective and some were ineffective like BCG, and their efficiency has not been established yet.

Subsequently, cell wall skeletons (CWS) as prepared from cell walls obtained by grinding BCG bacterial cells and then fractionating the same by centrifugation, were used as immunotherapeutic agents in order to prevent side effects and make improvements in terms of dose and frequency of inoculation. Yamamura et al. of Osaka University and their coworkers conducted clinical trials for pulmonary cancer, leukemia, stomach cancer and the like under randomized design using BCG-CWS and N. rubra-CWS. The results were not satisfied although stochastically significant prolongation of survival time was shown, thus the therapy with CWS being not practically utilized.

The inventor of the present application suspected the efficacy of the combined therapy of an immunotherapy with a conventional cancer therapy such as chemotherapy in 1970's, and conducted an immunotherapy independently after eradicating cancer cells as much as possible. As the results, the inventor obtained excellent results that have not been ever obtained (Proc. Japan Acad., 74, Ser. B, 50–55, 1998). This demonstrates that the immunotherapy with BCG-CWS is effective only on patients who retain a normal immunocompetence, and even independently provides direct effectiveness on human cancers. In other words, this also shows that the immune suppression effected by the conventional chemotherapies and radiotherapies results from the eradicating of the primary efficacy of immunotherapies. Also, this fact explicitly describes the ground for the lowered efficacy of immunotherapies on patients with highly-advanced cancers. Specifically, patients with highly-advanced cancers, who are extremely decreased in immunocompetence, should not be applied to immunotherapies, which constitutes the limited utility of immunotherapies.

On the other hand, contrary to the fact that adoptive immunity in vertebrates and other higher species has been interested in conventional immunology, innate immunity recently has been recognized as defense mechanism effective in more animals in the living world (Cold Spring Harbor Symp. Quant. Biol., 54, 1–13, 1989. Cell, 91, 295–298, 1997). The immunotherapy with independent use of BCG-CWS that has been demonstrated to provide excellent clinical results on cancer patients by the inventor for the first time correspond to such a new trend in immunology, and is considered to cause basic human defense system against not only cancers but also the whole of foreign materials, which should be significance of existence of the immunotherapy.

INDUSTRIAL APPLICABILITY

The invention of the present application relates to an immunotherapeutic agent for a cancer and/or a microbial infection which comprises a bacterial component as an effective ingredient, and specifically, to an immunotherapeutic agent for a cancer which excellently improves immunocompetence of a patient, wherein said agent is independently used without any other chemotherapeutic agent, and is combined with a non-radical lymphadenectomy in the treatment of cancers.

According to the invention, an immunotherapy for cancer that is more effective than conventional therapies, and an immunotherapy for various infections have been realized.

The invention in which lymph nodes are not totally removed may cause disadvantages including the remaining of a metastatic lymph node that is a risk factor for a patient, but the disadvantage should be considered to be decreased by bacterial components that significantly improve the therapeutic effects according to the invention. Specifically, immunocompetence in healthy conditions wherein Innate-Adaptive immunity by lymph nodes is completely intact is maintained as it is, and suppresses the reoccurrence. Further, lymph ducts connecting to lymph nodes are also retained, and therefore the network interfacing between lymph nodes via lymph ducts is maintained as it is. Also, aftereffects such as edema or dysmobility that are associated with radical lymphadenectomy are not arisen. Furthermore, the invention makes it easier for physicians to conduct surgical operations.

The invention claimed is:
1. A method for treating cancer, which comprises:
   administering a pharmaceutical composition comprising a bacterial cell wall skeleton as an effective ingredient to a patient in need thereof,
   wherein said pharmaceutical composition is administered concurrently with a surgical operation to remove a cancer-carrying tissue, and
   wherein the surgical operation comprises a non-radical lymphadenectomy in which lymph nodes are not removed.
2. The method according to claim 1, wherein the bacterial cell wall skeleton is BCG-CWS.
3. The method according to claim 1, wherein the cancer is ovarian cancer, breast cancer or cervical cancer.
4. The method according to claim 1, which further comprises:
   (a) administering the pharmaceutical composition before conducting the surgical operation;
   (b) conducting the surgical operation;
   (c) administering the pharmaceutical composition after the surgical operation.

* * * * *